(12) United States Patent
Shadeck et al.

(10) Patent No.: US 8,545,527 B2
(45) Date of Patent: *Oct. 1, 2013

(54) CONTROL FOR A POWERED SURGICAL INSTRUMENT

(75) Inventors: Louis M. Shadeck, Jacksonville, FL (US); Vikram Mullick, Amsterdam, NY (US); Manfred Luedi, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/468,079

(22) Filed: May 10, 2012

(65) Prior Publication Data

US 2012/0221028 A1 Aug. 30, 2012

Related U.S. Application Data

(63) Continuation of application No. 12/052,549, filed on Mar. 20, 2008, now Pat. No. 8,197,501.

(51) Int. Cl.
*A61B 17/32* (2006.01)
*B23B 45/00* (2006.01)

(52) U.S. Cl.
USPC .............................................. 606/167; 408/9

(58) Field of Classification Search
USPC .......... 74/479.01, 491, 512–514, 560; 408/8, 408/9; 604/22; 606/1, 167, 169, 170, 180
See application file for complete search history.

(56) References Cited

U.S. PATENT DOCUMENTS

| 4,552,143 A | 11/1985 | Lottick |
| 4,768,496 A | 9/1988 | Kreizman et al. |
| 5,017,354 A | 5/1991 | Simms et al. |
| 5,217,478 A | 6/1993 | Rexroth |
| 5,421,829 A | 6/1995 | Olichney et al. |
| 5,478,093 A | 12/1995 | Eibl et al. |
| 5,484,398 A | 1/1996 | Stoddard |
| 5,543,695 A | 8/1996 | Culp et al. |
| 5,685,838 A | 11/1997 | Peters et al. |

(Continued)

FOREIGN PATENT DOCUMENTS

| EP | 0555105 A1 | 8/1993 |
| JP | 06014876 | 1/1994 |

(Continued)

OTHER PUBLICATIONS

International Search Report mailed Jun. 22, 2009 for PCT/US2009/036460 claiming benefit of U.S. Appl. No. 12/052,549, filed Mar. 20, 2008.

(Continued)

*Primary Examiner* — Ryan Severson
*Assistant Examiner* — Ashley Fishback
(74) *Attorney, Agent, or Firm* — Harness, Dickey

(57) ABSTRACT

A surgical instrument is provided for cutting bone and other tissue. The instrument includes a housing. A plurality of sensors is located in the housing in a spaced apart orientation from each other. A collar is moveably mounted to the housing into a plurality of different collar orientations on the housing. A lever comprising an actuator is moveably coupled to the collar and, with the collar located in any one of the plurality of different collar orientations, the lever is operable to move the actuator relative to one of the plurality of sensors in order to vary a signal produced by that sensor.

20 Claims, 20 Drawing Sheets

(56) References Cited

U.S. PATENT DOCUMENTS

| | | |
|---|---|---|
| 5,712,543 A | 1/1998 | Sjostrom |
| 5,720,742 A | 2/1998 | Zacharias |
| 5,871,493 A | 2/1999 | Sjostrom et al. |
| 5,951,581 A | 9/1999 | Saadat et al. |
| 5,957,881 A | 9/1999 | Peters et al. |
| 5,971,012 A | 10/1999 | Skoglund |
| 6,007,540 A | 12/1999 | Ark |
| 6,017,354 A | 1/2000 | Culp et al. |
| 6,037,724 A | 3/2000 | Buss et al. |
| 6,050,989 A | 4/2000 | Fox et al. |
| 6,090,120 A | 7/2000 | Wright et al. |
| 6,090,123 A | 7/2000 | Culp et al. |
| 6,117,152 A | 9/2000 | Huitema |
| 6,200,311 B1 | 3/2001 | Danek et al. |
| 6,299,591 B1 | 10/2001 | Banko |
| 6,328,752 B1 | 12/2001 | Sjostrom et al. |
| 6,329,778 B1 | 12/2001 | Culp et al. |
| 6,436,067 B1 | 8/2002 | Deng et al. |
| 6,451,022 B2 | 9/2002 | Dinger et al. |
| 6,500,169 B1 | 12/2002 | Deng |
| 6,508,823 B1 | 1/2003 | Gonon |
| 6,537,280 B2 | 3/2003 | Dinger et al. |
| 6,610,066 B2 | 8/2003 | Dinger et al. |
| 6,679,899 B2 | 1/2004 | Wiener et al. |
| 6,695,847 B2 | 2/2004 | Bianchetti et al. |
| 6,758,842 B2 | 7/2004 | Irion et al. |
| 6,761,698 B2 | 7/2004 | Shibata et al. |
| 6,786,897 B2 | 9/2004 | Mc Ie et al. |
| 6,793,490 B2 | 9/2004 | Bianchetti et al. |
| 6,840,948 B2 | 1/2005 | Albrecht et al. |
| 6,929,476 B2 | 8/2005 | Katsuda et al. |
| 6,945,981 B2 | 9/2005 | Donofrio et al. |
| 6,958,071 B2 | 10/2005 | Carusillo et al. |
| 6,969,387 B2 | 11/2005 | Yamamoto |
| 7,022,128 B2 | 4/2006 | Morawski et al. |
| 7,063,692 B2 | 6/2006 | Sakurai et al. |
| 8,197,501 B2 | 6/2012 | Shadeck et al. |
| 2001/0004695 A1 | 6/2001 | Vercellotti et al. |
| 2001/0039427 A1 | 11/2001 | Dinger et al. |
| 2001/0039428 A1 | 11/2001 | Dinger et al. |
| 2001/0047183 A1 | 11/2001 | Privitera et al. |
| 2002/0087179 A1 | 7/2002 | Culp et al. |
| 2002/0156466 A1 | 10/2002 | Sakurai et al. |
| 2002/0182564 A1 | 12/2002 | Katsuda et al. |
| 2003/0009166 A1 | 1/2003 | Moutafis et al. |
| 2003/0036747 A1 | 2/2003 | Ie et al. |
| 2003/0093088 A1 | 5/2003 | Long et al. |
| 2003/0093103 A1 | 5/2003 | Malackowski et al. |
| 2003/0135151 A1 | 7/2003 | Deng |
| 2004/0010258 A1 | 1/2004 | Carusillo et al. |
| 2004/0059363 A1 | 3/2004 | Alvarez et al. |
| 2004/0092991 A1 | 5/2004 | Deng |
| 2004/0092992 A1 | 5/2004 | Adams et al. |
| 2004/0102782 A1 | 5/2004 | Vercellotti et al. |
| 2004/0220602 A1 | 11/2004 | Deng et al. |
| 2004/0225310 A1 | 11/2004 | Culp et al. |
| 2005/0015104 A1 | 1/2005 | Morawski et al. |
| 2005/0049546 A1 | 3/2005 | Messerly et al. |
| 2005/0085798 A1 | 4/2005 | Hofmann et al. |
| 2005/0085838 A1 | 4/2005 | Thompson et al. |
| 2005/0142515 A1 | 6/2005 | Levy et al. |
| 2005/0222587 A1 | 10/2005 | Jinno et al. |
| 2005/0245910 A1 | 11/2005 | Wright et al. |
| 2005/0245911 A1 | 11/2005 | Wright et al. |
| 2005/0245912 A1 | 11/2005 | Murphy et al. |
| 2005/0277970 A1 | 12/2005 | Norman et al. |
| 2005/0283150 A1 | 12/2005 | Moutafis et al. |
| 2006/0020282 A1 | 1/2006 | Henniges et al. |
| 2006/0047271 A1 | 3/2006 | McPherson et al. |
| 2006/0047272 A1 | 3/2006 | McPherson et al. |
| 2006/0089622 A1 | 4/2006 | Bourne et al. |
| 2006/0206100 A1 | 9/2006 | Eskridge et al. |
| 2007/0078301 A1 | 4/2007 | Kura et al. |

FOREIGN PATENT DOCUMENTS

| | | |
|---|---|---|
| JP | 2000-507839 | 6/2000 |
| JP | 2007105485 | 4/2007 |
| JP | 2007195993 | 8/2007 |
| WO | WO-2009117266 A1 | 9/2009 |

OTHER PUBLICATIONS

International Preliminary Report on Patentability mailed Sep. 30, 2010 for PCT/US2009/036460 claiming benefit of U.S. Appl. No. 12/052,549, filed Mar. 20, 2008.

Office Action mailed Jul. 1, 2013 for Japanese Application No. 2011-500862 for corresponding PCT/US2009/036460 filed Mar. 9, 2009 claiming benefit of U.S. Appl. No. 12/052,549, filed Mar. 20, 2008 (1 page).

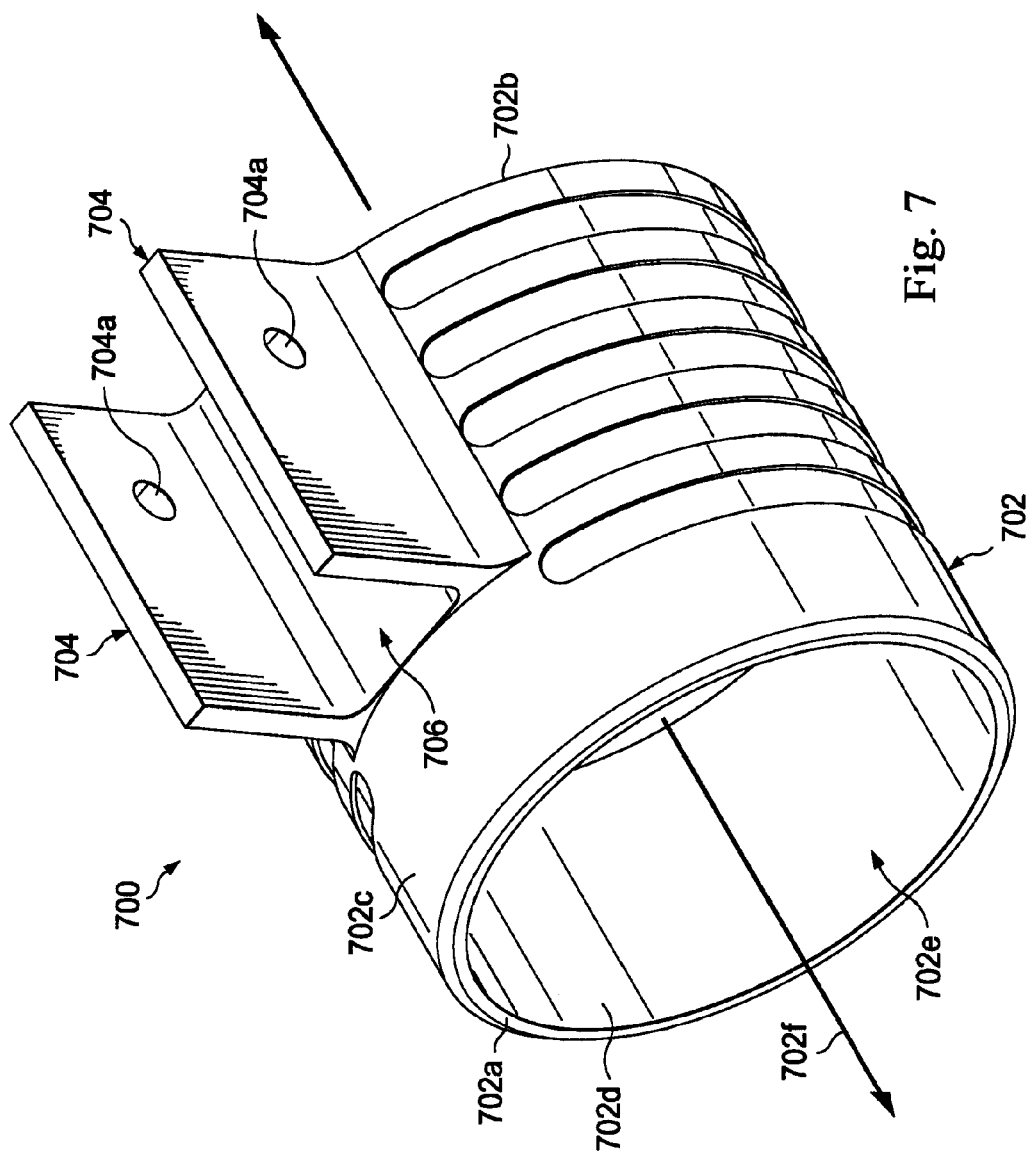

CONTROL FOR A POWERED SURGICAL INSTRUMENT

PRIORITY

The present application is a continuation of, and claims priority to U.S. patent application Ser. No. 12/052,549, filed Mar. 20, 2008, now U.S. Pat. No. 8,197,501 issued on Jun. 12, 2012, which is incorporated herein by reference.

FIELD OF THE INVENTION

The present disclosure generally relates to surgical instruments and in particular to surgical instruments for dissecting bone and other tissue.

BACKGROUND

Surgical instruments may use a variety of methods to control the operating speed of the instrument. For example, a powered surgical instrument used for dissecting bone or tissue may use a control lever that may be moved to increase or decrease the operating speed of the instrument.

Difficulties may arise in the control of the powered surgical instrument. Some conventional powered surgical instruments include the control lever fixed to the instrument. The control lever may be resiliently and pivotally coupled to the instrument such that a user may pivot the control lever towards the instrument to increase the operating speed, and then allow the control lever to resiliently pivot away from the instrument to decrease the operating speed. However, in some situations, the control lever may be interfered with by, for example, angled cutting attachments that are coupled to and powered by the powered surgical instrument, wires, pins, fixtures, and a variety of other obstructions known in the art. In addition, the fixed position of the control lever may result in wrist and/or hand fatigue to the user.

Therefore, what is needed is an improved control for a surgical instrument.

SUMMARY

The present disclosure provides many technological advances that can be used, either alone or in combination, to provide an improved control for a powered surgical instrument and/or an improved system and method for controlling powered surgical instruments.

In one embodiment, a surgical instrument includes a housing, a plurality of sensors located in the housing in a spaced apart orientation from each other, a collar moveably mounted to the housing into a plurality of different collar orientations on the housing; and a lever comprising an actuator and moveably coupled to the collar, wherein, with the collar located in any one of the plurality of different collar orientations, the lever is operable to move the actuator relative to one of the plurality of sensors in order to vary a signal produced by that sensor.

Further forms and embodiments will become apparent from the detailed description provided hereinafter. It should be understood that the detailed description and specific examples, while indicating preferred embodiments, are intended for purposes of illustration only and are not intended to be limiting.

BRIEF DESCRIPTION OF THE DRAWINGS

The present disclosure will become more fully understood from the detailed description and the accompanying drawings, wherein:

FIG. 1b is a perspective view illustrating an embodiment of the surgical instrument of FIG. 1a.

FIG. 1c is a perspective, cross sectional view illustrating an embodiment of the surgical instrument of FIG. 1a.

FIG. 1d is a perspective, cross sectional view illustrating an embodiment of the surgical instrument of FIG. 1a.

FIG. 2b is a cross sectional view illustrating an embodiment of the backnut of FIG. 2a.

FIG. 3b is a front perspective view illustrating an embodiment of the connector insert of FIG. 3a.

FIG. 7 is a perspective view illustrating an embodiment of a collar used with the surgical instrument of FIGS. 1a, 1b, 1c, and 1d.

FIG. 8b is a rear view illustrating an embodiment of the press ring of FIG. 8a.

FIG. 9b is a cross sectional view illustrating an embodiment of the lever of FIG. 9a.

DETAILED DESCRIPTION

Figure 1A:
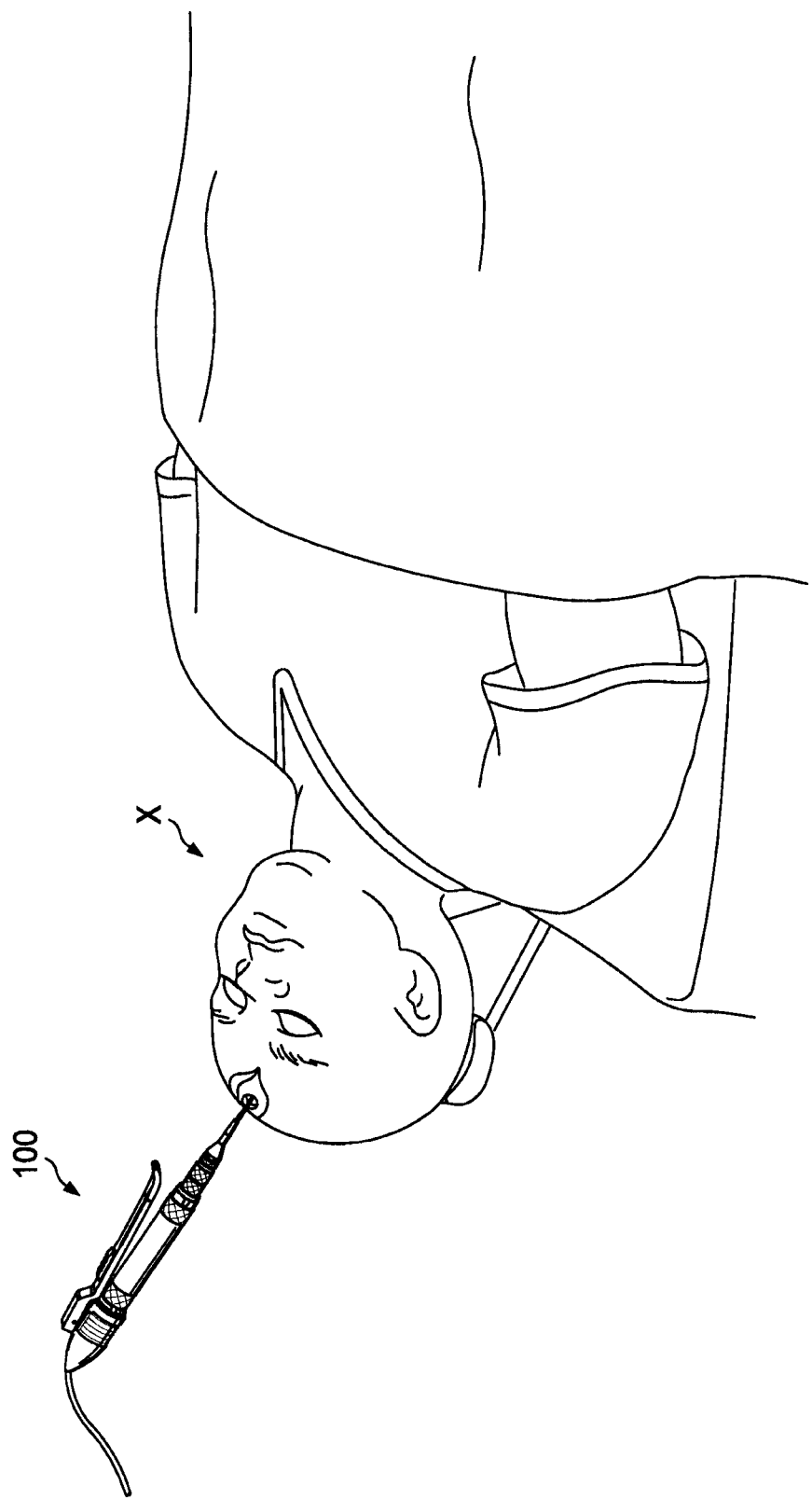
FIG. 1a is an environmental view illustrating an embodiment of a surgical instrument for the dissection of bone and other tissue according to the teachings of an embodiment of the present disclosure operatively associated with a patient undergoing a craniotomy procedure.

The present disclosure relates to surgical tools, and more particularly, to a control for use in powered surgical instruments. It is understood, however, that the following disclosure provides many different embodiments, or examples, for implementing different features of the control. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

Referring initially to FIG. 1a, a surgical instrument for the dissection of bone and other tissue constructed in accordance with the teachings of a first preferred embodiment of the present disclosure is illustrated and generally identified at reference numeral 100. The surgical instrument 100 is shown operatively associated with a patient X for performing a craniotomy. It will become apparent to those skilled in the art that the subject invention is not limited to any particular surgical application but has utility for various applications in which it is desired to dissect bone or other tissue.

Figure 1B:
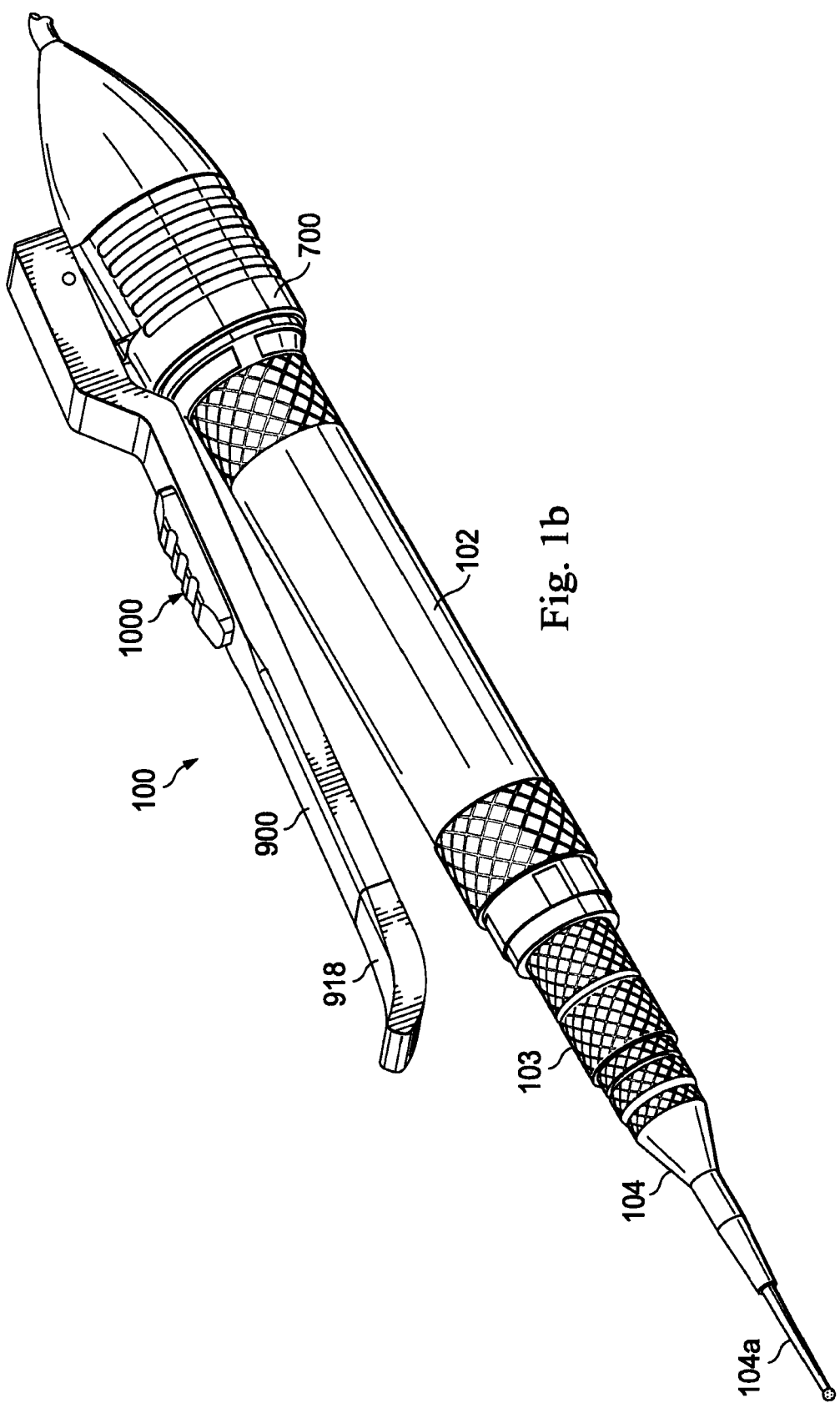
Figure 1C:
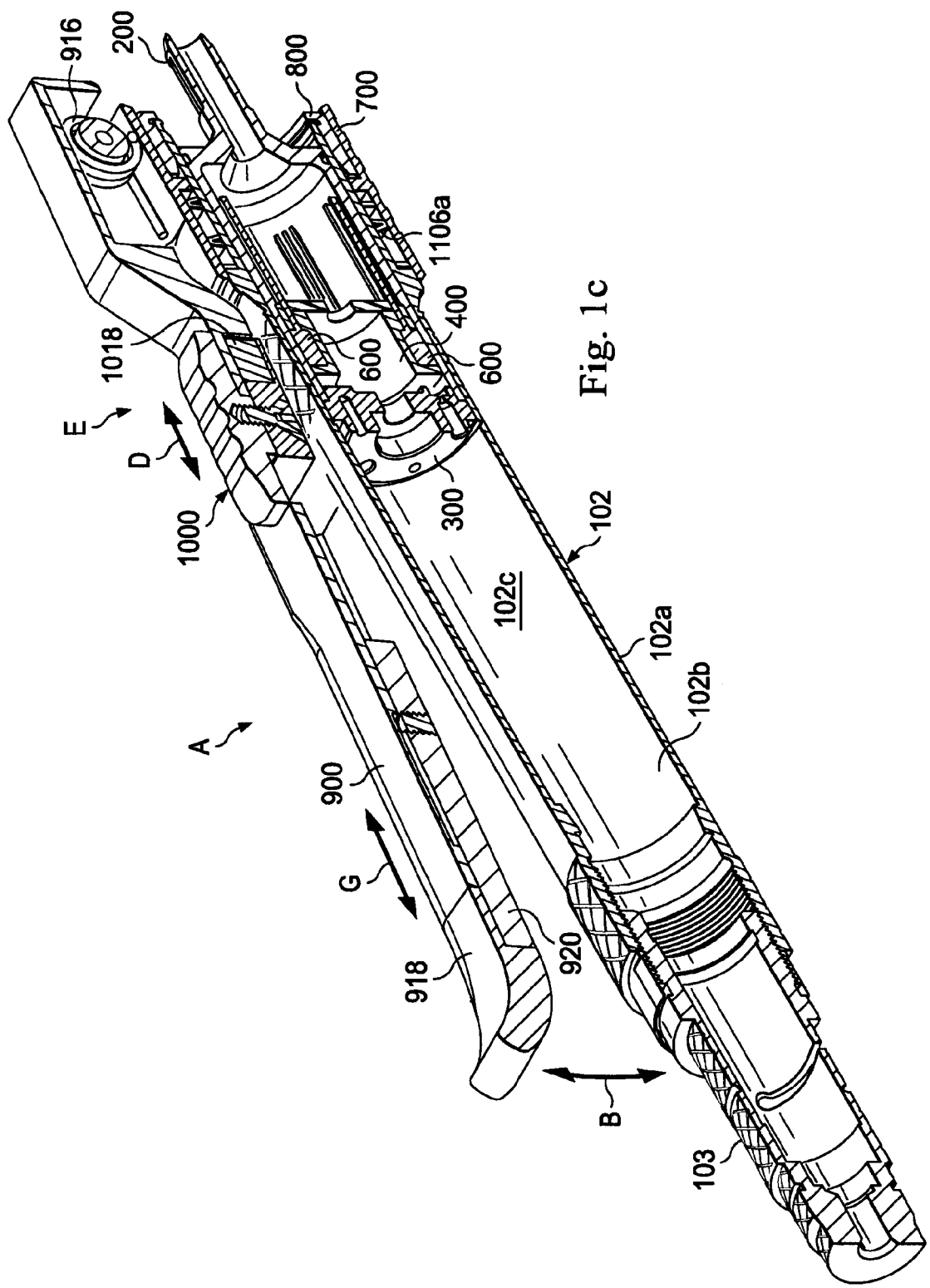
Figure 1D:
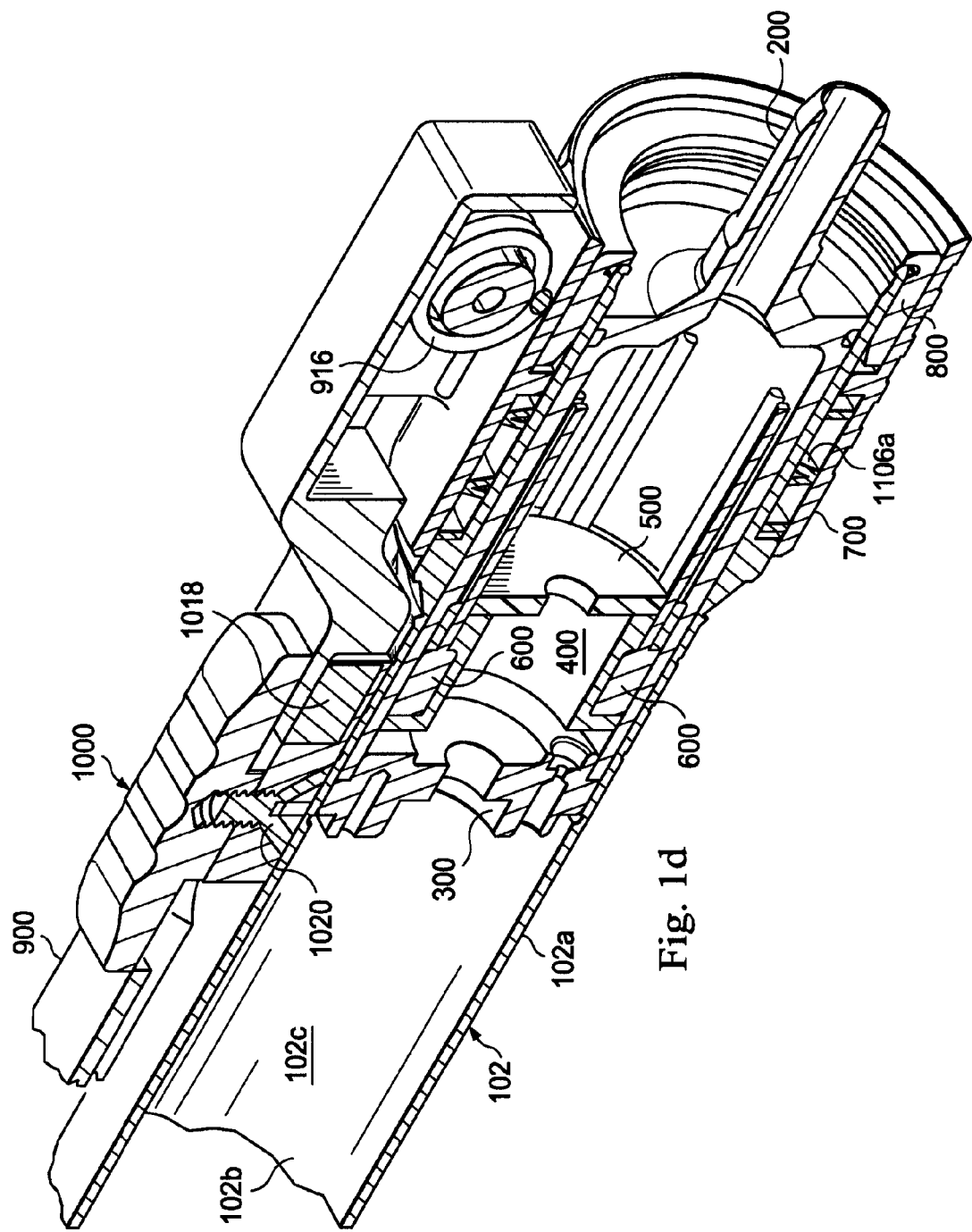
Figure 2A:
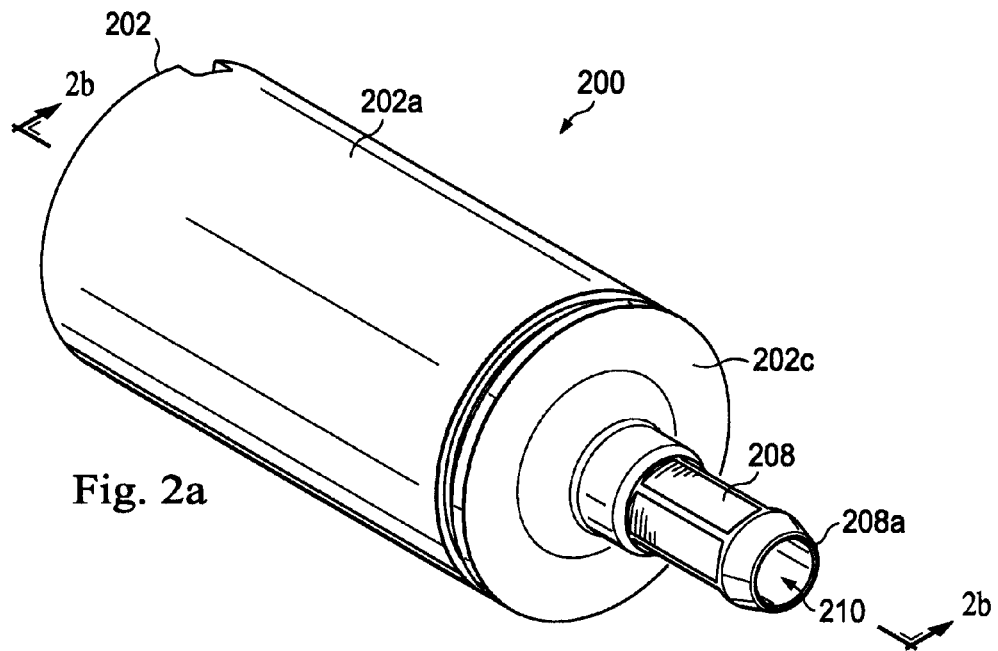
FIG. 2a is a perspective view illustrating an embodiment of a backnut used with the surgical instrument of FIGS. 1a, 1b, 1c, and 1d.
Figure 2B:
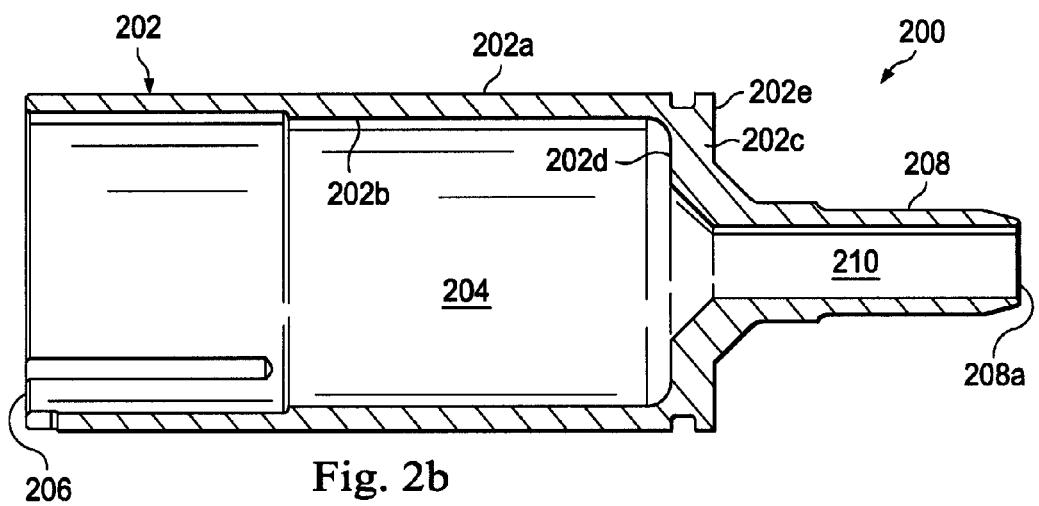
Figure 3A:
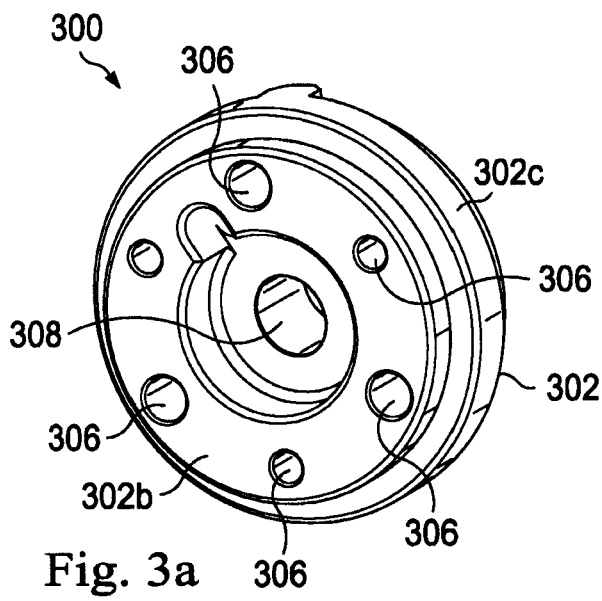
FIG. 3a is a rear perspective view illustrating an embodiment of a connector insert used with the surgical instrument of FIGS. 1a, 1b, 1c, and 1d.
Figure 3B:
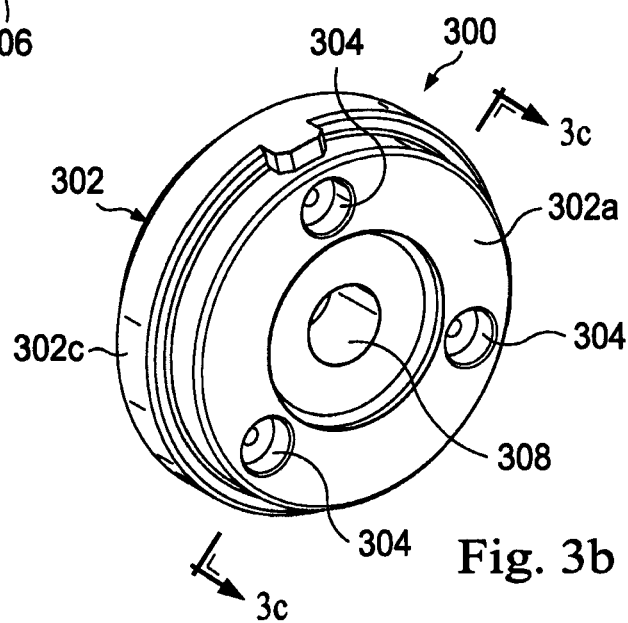
Figure 3C:
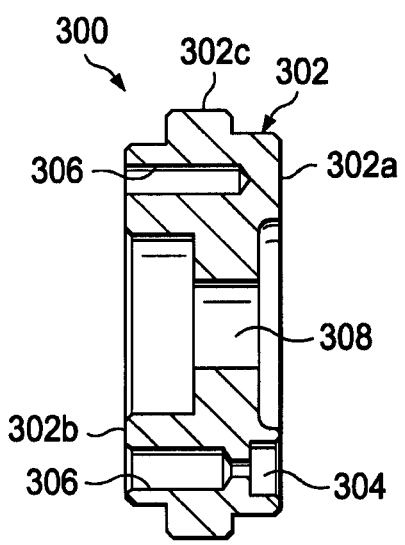
FIG. 3c is a cross sectional view illustrating an embodiment of the connector insert of FIGS. 3a and 3b.
Figure 4:
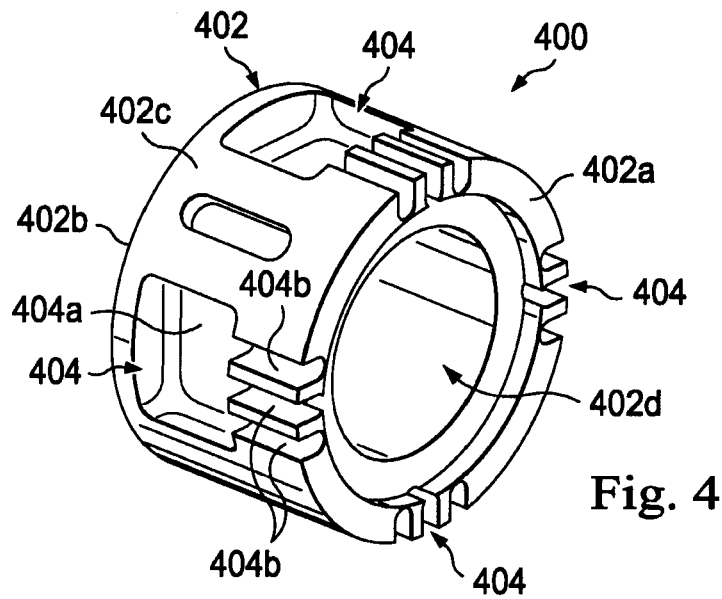
FIG. 4 is a perspective view illustrating an embodiment of a sensor ring used with the surgical instrument of FIGS. 1a, 1b, 1c, and 1d.
Figure 5:
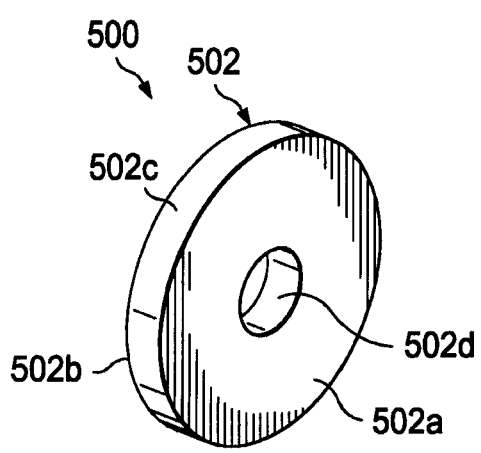
FIG. 5 is a perspective view illustrating an embodiment of a board used with the surgical instrument of FIGS. 1a, 1b, 1c, and 1d.
Figure 6:
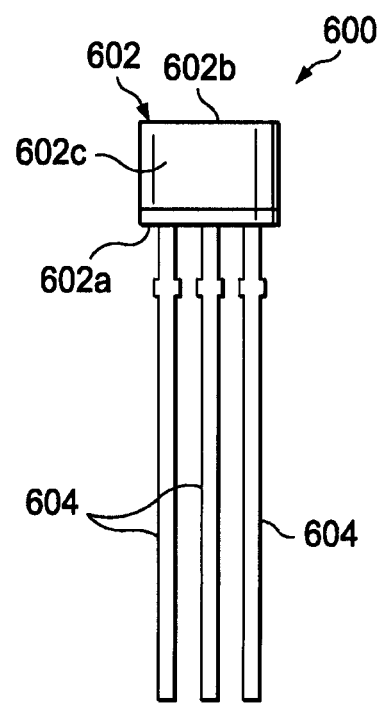
FIG. 6 is a bottom view illustrating an embodiment of a sensor used with the surgical instrument of FIGS. 1a, 1b, 1c, and 1d.
Figure 8A:
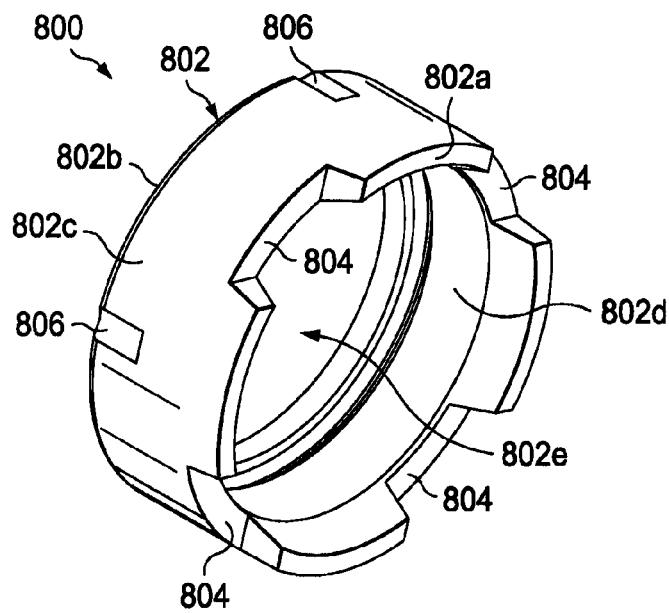
FIG. 8a is a perspective view illustrating an embodiment of a press ring used with the surgical instrument of FIGS. 1a, 1b, 1c, and 1d.
Figure 8B:
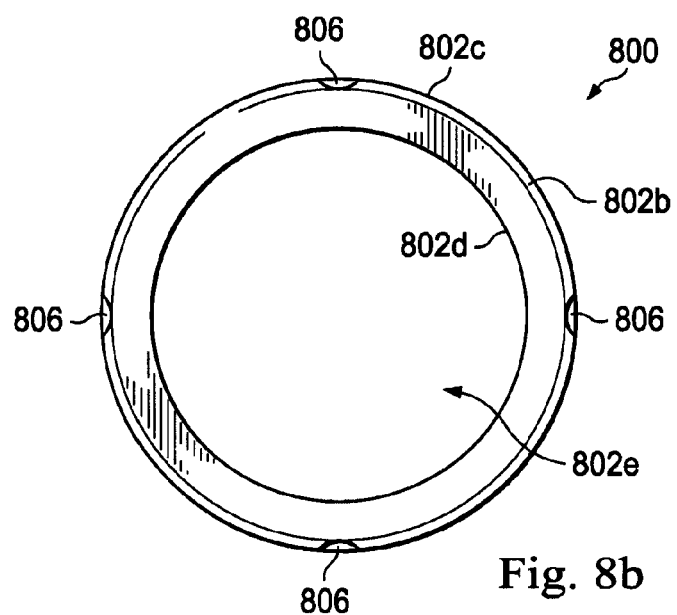
Figure 9A:
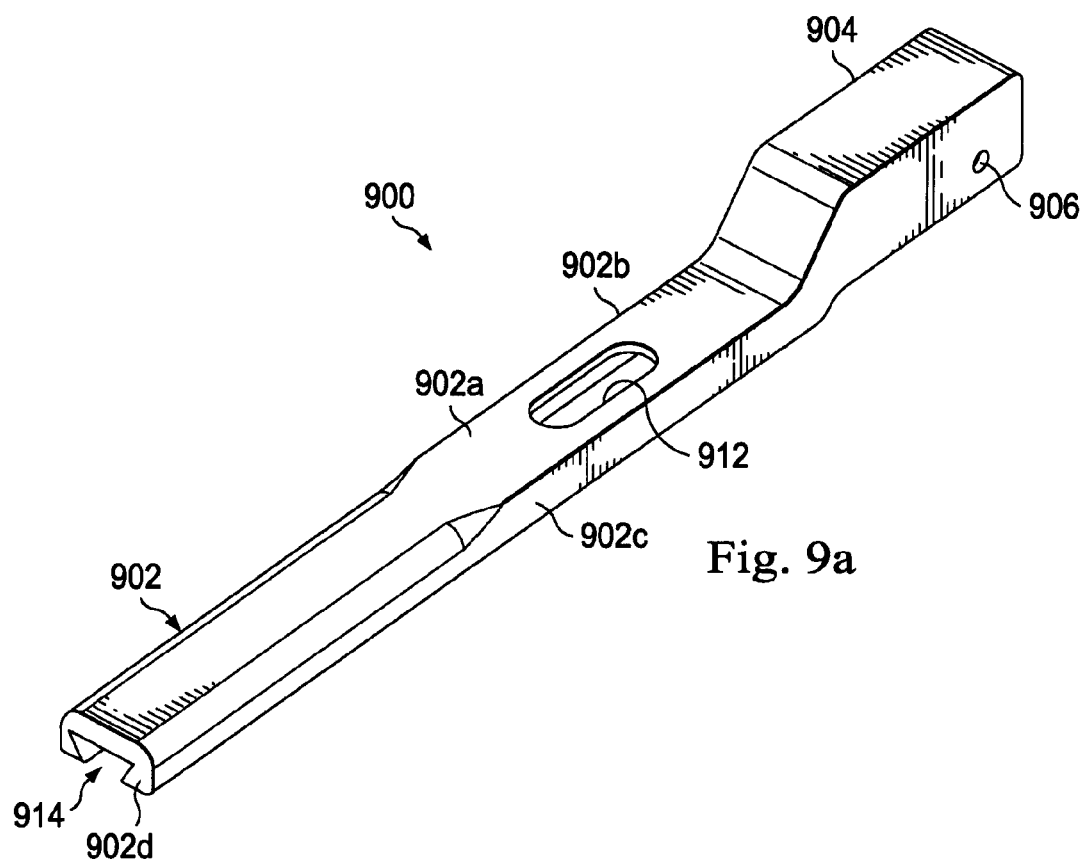
FIG. 9a is a perspective view illustrating an embodiment of a lever used with the surgical instrument of FIGS. 1a, 1b, 1c, and 1d.
Figure 9B:
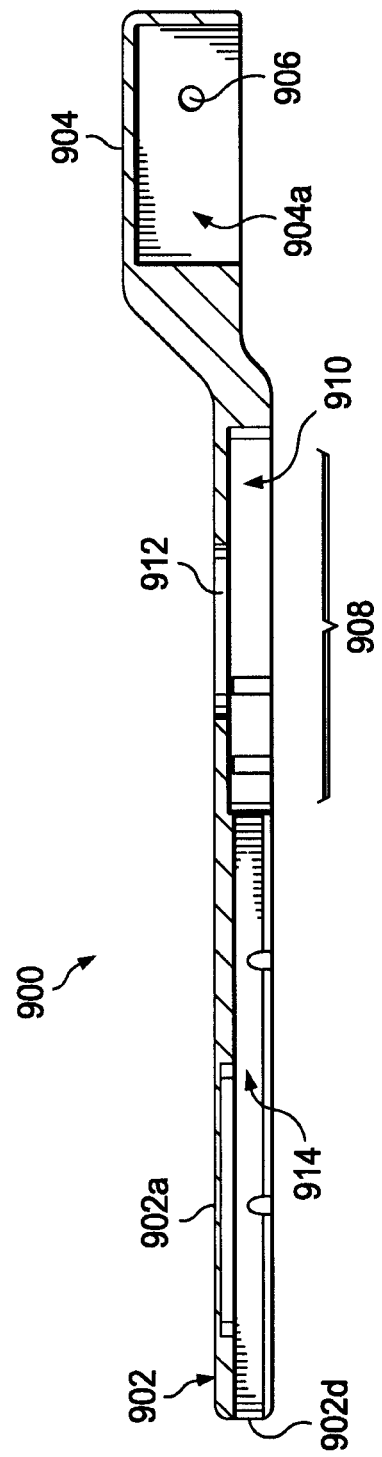
Figure 10A:
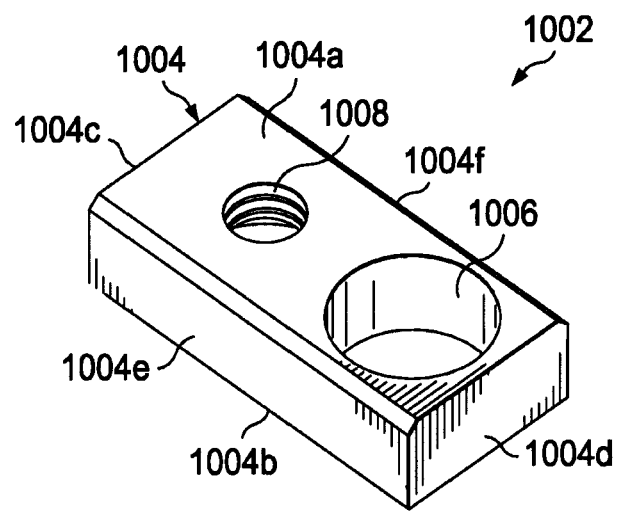
FIG. 10a is a perspective view illustrating an embodiment of an actuator holder used with the surgical instrument of FIGS. 1a, 1b, 1c, and 1d.
Figure 10B:
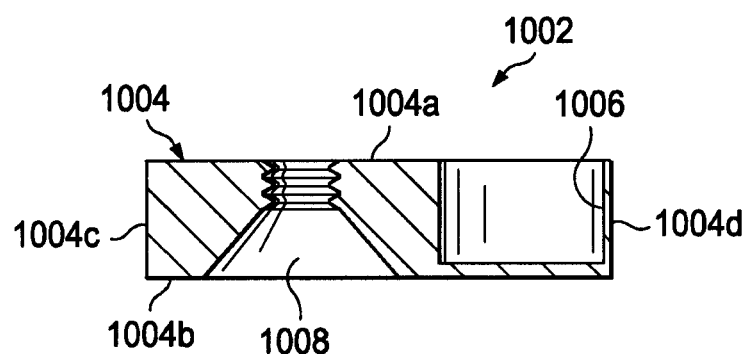
FIG. 10b is a cross sectional view illustrating an embodiment of the actuator holder of FIG. 10.
Figure 10C:
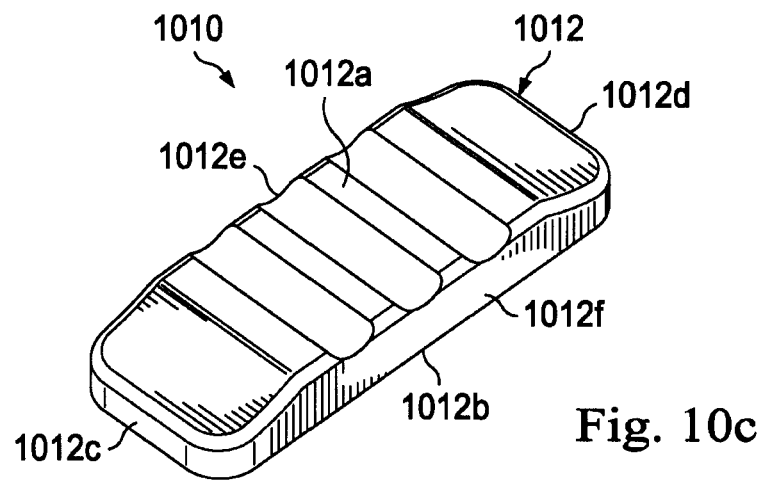
FIG. 10c is a perspective view illustrating an embodiment of an engagement member used with the surgical instrument of FIGS. 1a, 1b, 1c, and 1d.
Figure 10D:
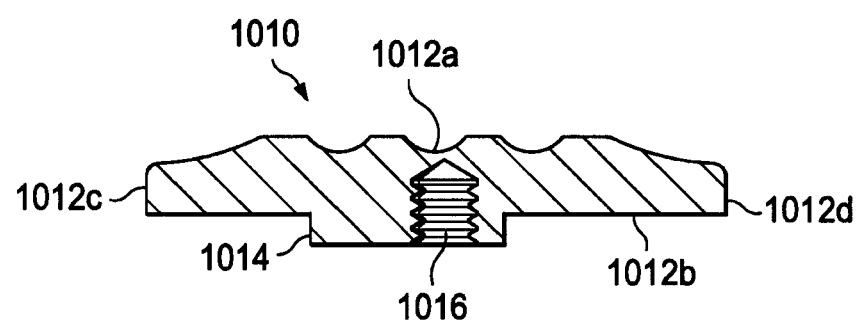
FIG. 10d is a cross sectional view illustrating an embodiment of the engagement member of FIG. 10c.

With reference to FIGS. 1b, 1c, and 1d, the surgical instrument 100 is illustrated to include a generally cylindrical housing 102 having an outer surface 102a, an inner surface 102b, and defining a housing volume 102c. A motor (not illustrated for clarity) may be housed in the housing volume 102c and may include a plurality of motor components. A coupling 103 couples a surgical attachment 104 to the housing 102. In the preferred embodiment, the surgical attachment 104 includes a cutting tool or dissection tool 104a, illustrated in FIG. 1b, that is coupled to the motor located in the housing volume 102c, although the type of tool is not essential to implementing the present invention. A distal end of the cutting tool 104a includes an element adapted for a particular procedure, such as a cutting element. The surgical attachment 104 may provide a gripping surface for use by a surgeon and may also shield underlying portions of the surgical instrument 100 during a surgical procedure. A plurality of components of a control for the surgical instrument 102 is coupled to the housing 102 and will be described in further detail below. The control components include a backnut 200, a connector insert 300, a sensor ring 400, a board 500, a plurality of sensors 600, a collar 700, a press ring 800, a lever 900, and a switch 1000.

Referring now to FIGS. 1b, 1c, 1d, 2a, and 2b, the backnut 200 is illustrated. The backnut 200 includes a generally cylindrical base 202 having an outer surface 202a, an inner surface 202b, and an endwall 202c having an inner surface 202d and an outer surface 202e opposite the inner surface 202d. A backnut volume 204 is defined by the base 202 between the inner surface 202b and the inner surface 202d of endwall 202c and includes a backnut volume entrance 206 located opposite the base 202 from the endwall 202c. A backnut member 208 extends from the outer surface 202e of the endwall 202c on the base 202, includes a distal end 208a and defines a passageway 210 extending from the distal end 208a to the backnut volume 204. The backnut 200 is located in the housing volume 102c of the housing 102 such that the outer surface 202a of the backnut 202 engages the inner surface 102b of the housing 102 and the backnut member 208 extends out of the housing, as illustrated in FIGS. 1c and 1d.

Referring now to FIGS. 1b, 1c, 1d, 3a, 3b, and 3c, the connector insert 300 is illustrated. The connector insert 300 includes a generally circular base 302 having a front surface 302a, a rear surface 302b, and an outer surface 302c extending between the front surface 302a and the rear surface 302b. A plurality of apertures 304 extend into the base 302 from the front surface 302a. A plurality of apertures 306 extend into the base 302 from the rear surface 302b. A passageway 308 extends through the base 302 from the front surface 302a to the rear surface 302b. The connector insert 300 is located in the housing volume 102 of the housing 102 such that the outer surface 302c of the connector insert 300 engages the inner surface 102b of the housing 102 and the front surface 302a of the connector insert 300 extends into the backnut volume 204 through the backnut volume entrance 206, as illustrated in FIGS. 1c and 1d.

Referring now to FIGS. 1b, 1c, 1d, 2b, and 4, the sensor ring 400 is illustrated. The sensor ring 400 includes a generally cylindrical base 402 having a front surface 402a, a rear surface 402b, and an outer surface 402c extending between the front surface 402a and the rear surface 402b. A passageway 402d is defined by the base 402 and extends through the base 402 from the front surface 402a to the rear surface 402b. A plurality of sensor channels 404 are defined by the base 402 and located in a spaced apart orientation on the outer surface 402c of the base 402. In an embodiment, each of the sensor channels 404 are substantially similar and include a sensor mounting channel 404a extending into the base 402 from the outer surface 402c and a plurality of lead channels 404b extending from the sensor mounting channel 404a to the front surface 402a of the base 402. In the illustrated embodiment, the sensor channels 404 are radially spaced apart from each other on the base 402 by approximately 90 degrees. However, the sensor channels 404 may be more or less in number, and may be spaced further apart or closer together at regular or irregular intervals. The sensor ring 400 is located in the backnut volume 204 adjacent the backnut volume entrance 206 and the front surface 302a of the connector insert 300 with the outer surface 402c of the sensor ring 400 engaging the inner surface 202b of the backnut 200, as illustrated in FIGS. 1c and 1d.

Referring now to FIGS. 1b, 1c, 1d, 2b, 4, and 5, the board 500 is illustrated. The board 500 includes a generally circular base 502 having a front surface 502a, a rear surface 502b, and an outer surface 502c extending between the front surface 502a and the rear surface 502b. A passageway 502d extends through the base 502a from the front surface 502a to the rear surface 502b. In an embodiment, the board 500 may be a printed circuit board and may include circuitry and/or circuit board components known in the art. The board 500 is located in the backnut volume 204 such that the rear surface 502b of the board 500 engages the front surface 402a of the sensor ring 400, as illustrated in FIGS. 1c and 1d.

Referring now to FIGS. 1b, 1c, 1d, 2b, 4, 5, and 6, one of the plurality of sensors 600 is illustrated. The sensor 600 includes a sensor member 602 having a front surface 602a, a rear surface 602b, and a bottom surface 602c extending between the front surface 602 and the rear surface 602b. A plurality of sensor leads 604 extend from the front surface 602a of the sensor member 602. In an embodiment, the sensor 600 is an A132x Ratiometric Linear Hall-Effect Sensor for High-Temperature Operation, available commercially from Allegro MicroSystems, Inc. 115 Northeast Cutoff, Worcester, Mass. 01615-0036. A sensor 600 is positioned in each of the sensor channels 404 such that the sensor member 602 is located in the sensor mounting channel 404a and the sensor leads 604 extend through the lead channels 404b and into engagement with the outer surface 502c and/or circuitry components of the board 500, as illustrated in FIGS. 1c and 1d. In an embodiment, the sensor leads 604 are coupled to circuitry on the board 500. With the sensors 600 positioned in the sensor channels 404, the sensors are located adjacent the inner surface 202b of the backnut 200 and the inner surface 102b of the housing 102 and are radially spaced apart from each other by approximately 90 degrees, as illustrated in FIGS. 1c and 1d.

Referring now to FIGS. 1b, 1c, 1d, 2b, and 7, the collar 700 is illustrated. The collar 700 includes a generally cylindrical base 702 having a front surface 702a, a rear surface 702b, an outer surface 702c extending between the front surface 702a and the rear surface 702b, and an inner surface 702d located opposite the outer surface 702c and extending between the front surface 702a and the rear surface 702b. A passageway 702e extends through the base 702 from the front surface 702a to the rear surface 702b. The collar 700 includes an axis 702f centrally located in the passageway 702c. A plurality of lever mounting members 704 extend from the outer surface of the base 702 adjacent the rear surface 702b in a spaced apart orientation from each other such that they define a channel 706 between them. Each of the lever mounting members 704 define a mounting aperture 704a. The collar 700 is mounted to the outer surface 102a of the housing 102 adjacent the backnut 200, as illustrated in FIGS. 1c, and 1d, such that the collar 700 is able to rotate about the housing 102 and the axis 702f, as will be described in further detail below.

Referring now to FIGS. 1b, 1c, 1d, 7, 8a, and 8b, the press ring 800 is illustrated. The press ring 800 includes a generally cylindrical base 802 having a front surface 802a, a rear surface 802b located opposite the front surface 802a, an outer surface 802c extending between the front surface 802a and the rear surface 802b, and an inner surface 802d located opposite the outer surface 802c and extending between the front surface 802a and the rear surface 802b. A passageway 802e extends through the base 802 from the front surface 802a to the rear surface 802b. In an embodiment, the press ring 800 is tapered towards the front surface 802a and includes a plurality of channels 804 defined along the front surface 802a and into the base 802. A plurality of indents 806 are defined by the base 802 in a radially spaced apart orientation, with each indent extending from the outer surface 802c to the rear surface 802b of the base 802. In an embodiment, the indents 806 are radially spaced apart at approximately 90 degree intervals. The press ring 800 is press fit to the outer surface 102a of the housing 102 between the housing 102 and the collar 700 such that the housing 102 is located in the passageway 802e defined by the press ring 800 with the inner surface 802d of the press ring 800 engaging the outer surface 102a of the housing 102, as illustrated in FIGS. 1c and 1d. With the press ring 800 press fit to the housing 102, the collar 700 is free to rotate about the housing 102 but may not be removed from the housing 102 without the use of a tool to remove the press ring 800. In an embodiment, the collar 700 includes features (not illustrated) that may engage the indents 806 on the press ring 800 in order to provide a plurality of different, discrete orientations in which, due to the engagement of those features and the indents 806, rotation of the collar 700 relative to the housing 102 is resisted.

Referring now to FIGS. 1b, 1c, 1d, 7, 9a, and 9b, the lever 900 is illustrated. The lever 900 includes an elongated base 902 having a top wall 902a and a pair of opposing side walls 902b and 902c extending from opposing sides of the top wall 902a. The top wall 902a and the sides walls 902b and 902c terminate at an end 902d. A collar mounting member 904 extends from an end of the base 902 opposite the end 902d and defines a collar housing 904a and a plurality of mounting apertures 906. The base 902 also includes a switch mounting region 908 that includes a switch mounting volume 910 defined between the top wall 902a and the side walls 902b and 902c and a switch mounting aperture 912 extending through the top wall 902a to the switch mounting region 910. An extendable distal end mounting volume 914 is also defined between the top wall 902a and the sides walls 902b and 902c and is located between the switch mounting volume 910 and the end 902d of the base 902. The lever 900 is pivotally coupled to the collar 700 by, for example, a rod extending through the mounting apertures 906 defined by the collar mounting member 904 on the lever 900 and the mounting apertures 704a defined by the lever mounting members 704 on the collar 700, as illustrated in FIGS. 1c and 1d. A resilient member 916 is located in the channel 706 defined by the lever mounting members 704 and engages the lever 900 and the collar 700 to resiliently bias the lever 900 away from the outer surface 102a of the housing 102, as illustrated in FIG. 1b and 1c. A distal end 918 includes a slidable coupling 920, illustrated in FIG. 1c, that is located in the extendable distal end mounting volume 914 and slidably coupled to the lever 900.

Referring now to FIGS. 1b, 1c, 1d, 9a, 9b, 10a, 10b, 10c, and 10d, the switch 1000 is illustrated. The switch 1000 includes an actuator holder 1002 that includes a base 1004 having a top surface 1004a, a bottom surface 1004b located opposite the top surface 1004a, a front surface 1004c extending between the top surface 1004a and the bottom surface 1004b, a rear surface 1004d located opposite the front surface 1004c and extending between the top surface 1004a and the bottom surface 1004b, and a pair of opposing side surfaces 1004e and 1004f extending between the top surface 1004a, the bottom surface 1004b, the front surface 1004c, and the rear surface 1004d. An actuator housing 1006 is defined by the base 1004, extends into the base 1004 from the top surface 1004a, and is located adjacent the rear surface 1004d. A fastener passageway 1008 is defined by the base 1004 and extends through the base 1004 from the top surface 1004a to the bottom surface 1004b. The switch 1000 also includes an engagement member 1010 that includes a base 1012 having a top surface 1012a, a bottom surface 1012b located opposite the top surface 1012a, a front surface 1012c extending between the top surface 1012a and the bottom surface 1012b, a rear surface 1012d located opposite the front surface 1012c and extending between the top surface 1012a and the bottom surface 1012b, and a pair of opposing side surfaces 1012e and 1012f extending between the top surface 1012a, the bottom surface 1012b, the front surface 1012c, and the rear surface 1012d. A guide member 1014 extends from the bottom surface 1012b of the base 1012, and the guide member 1014 and the base 1012 define a fastener aperture 1016 extending through the guide member 1014 and into the base 1012. In the illustrated embodiment, the fastener aperture 1016 is threaded. An actuator 1018, illustrated in FIGS. 1c and 1d, may be positioned in the actuator holder 1006. In an embodiment, the actuator 1018 may be, for example, a magnet, a samarium cobalt magnet, and/or a variety of other actuators known in the art. The switch 1000 is moveably coupled to the lever 900 by positioning the actuator holder 1002 in the switch mounting volume 910 and positioning the engagement member 1010 adjacent the top wall 902a of the lever 900 such that the guide member 1014 on the engagement member 1010 extends through the switch mounting aperture 912 defined by the lever 900. A fastener 1020 is then positioned in the fastener passageway 1008 defined by the actuator holder 1002 and engaged with the fastener aperture 1016 defined by the engagement member 1010 to coupled the switch 1000 to the lever 900. With the switch 1000 coupled to the lever 900, the switch 1000 may slidingly move relative to the lever 900 in the switch mounting aperture 912.

Figure 11A:
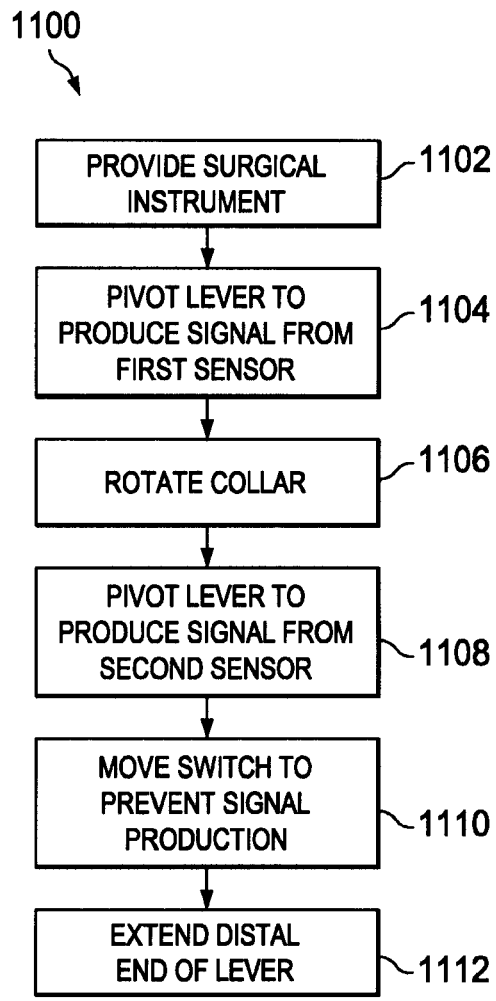
FIG. 11a is a flow chart illustrating an embodiment of a method for controlling a surgical instrument.
Figure 11B:
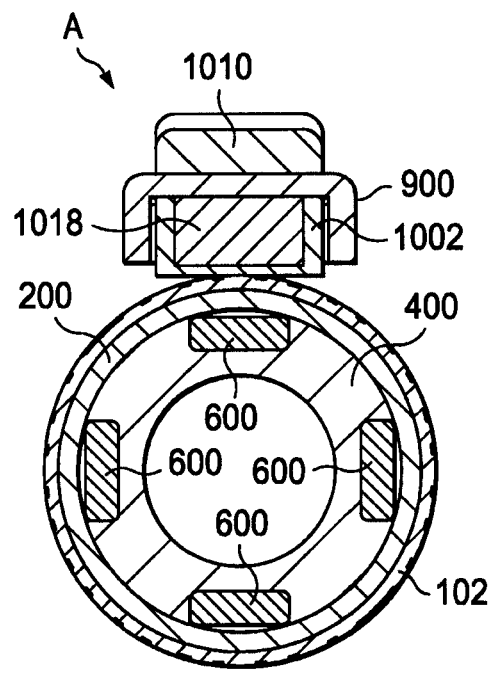
FIG. 11b is a cross sectional view illustrating an embodiment of the lever pivoted towards the housing on the surgical instrument with the collar in a first collar orientation.
Figure 11D:
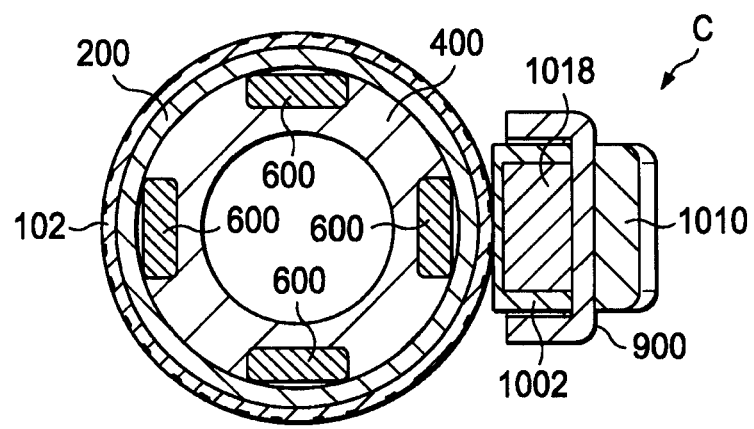
FIG. 11d is a cross sectional view illustrating an embodiment of the lever pivoted towards the housing on the surgical instrument with the collar in a second collar orientation.
Figure 11C:
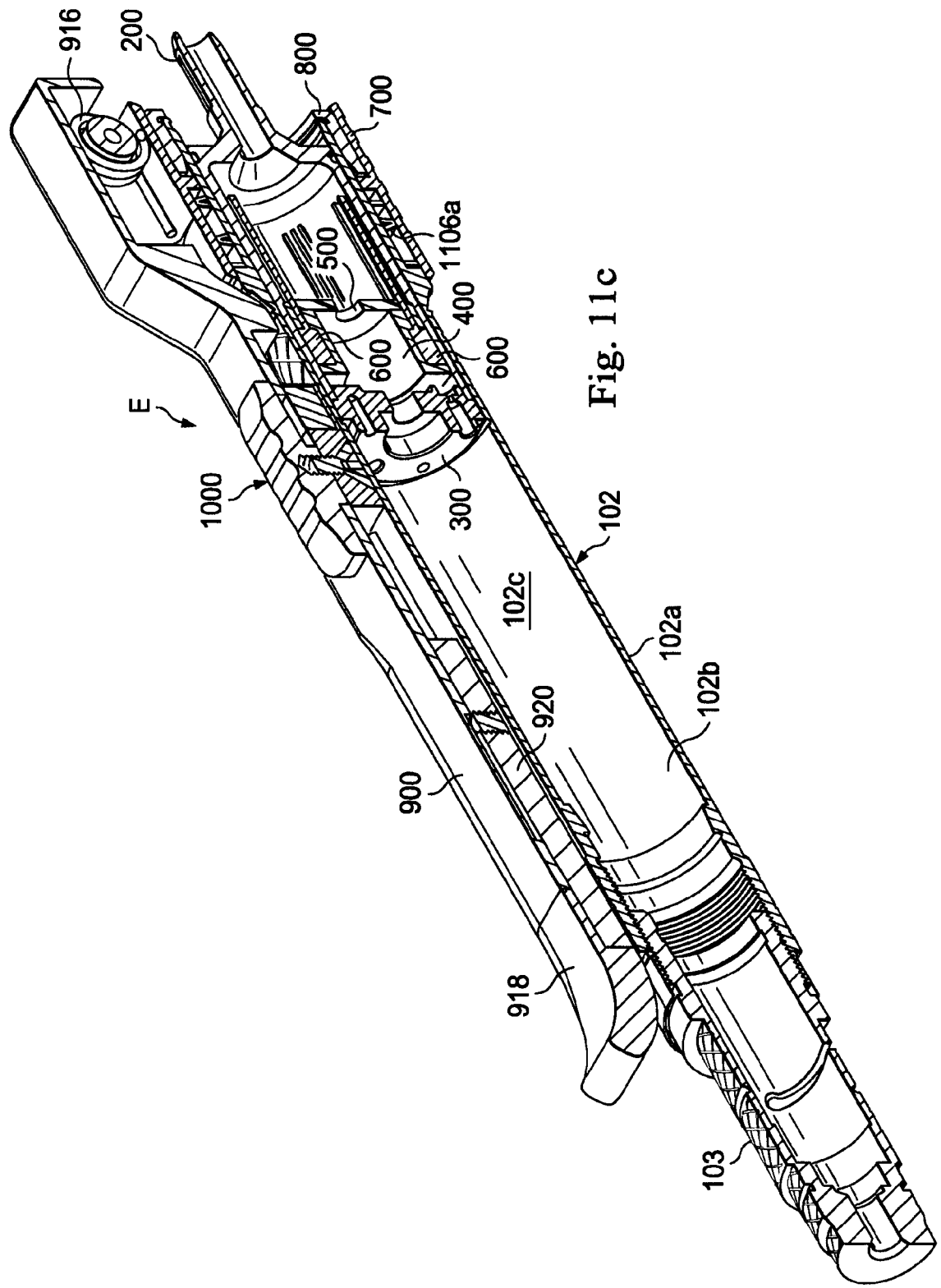
FIG. 11c is a perspective, cross sectional view illustrating an embodiment of the lever pivoted towards the housing on the surgical instrument.
Figure 11E:
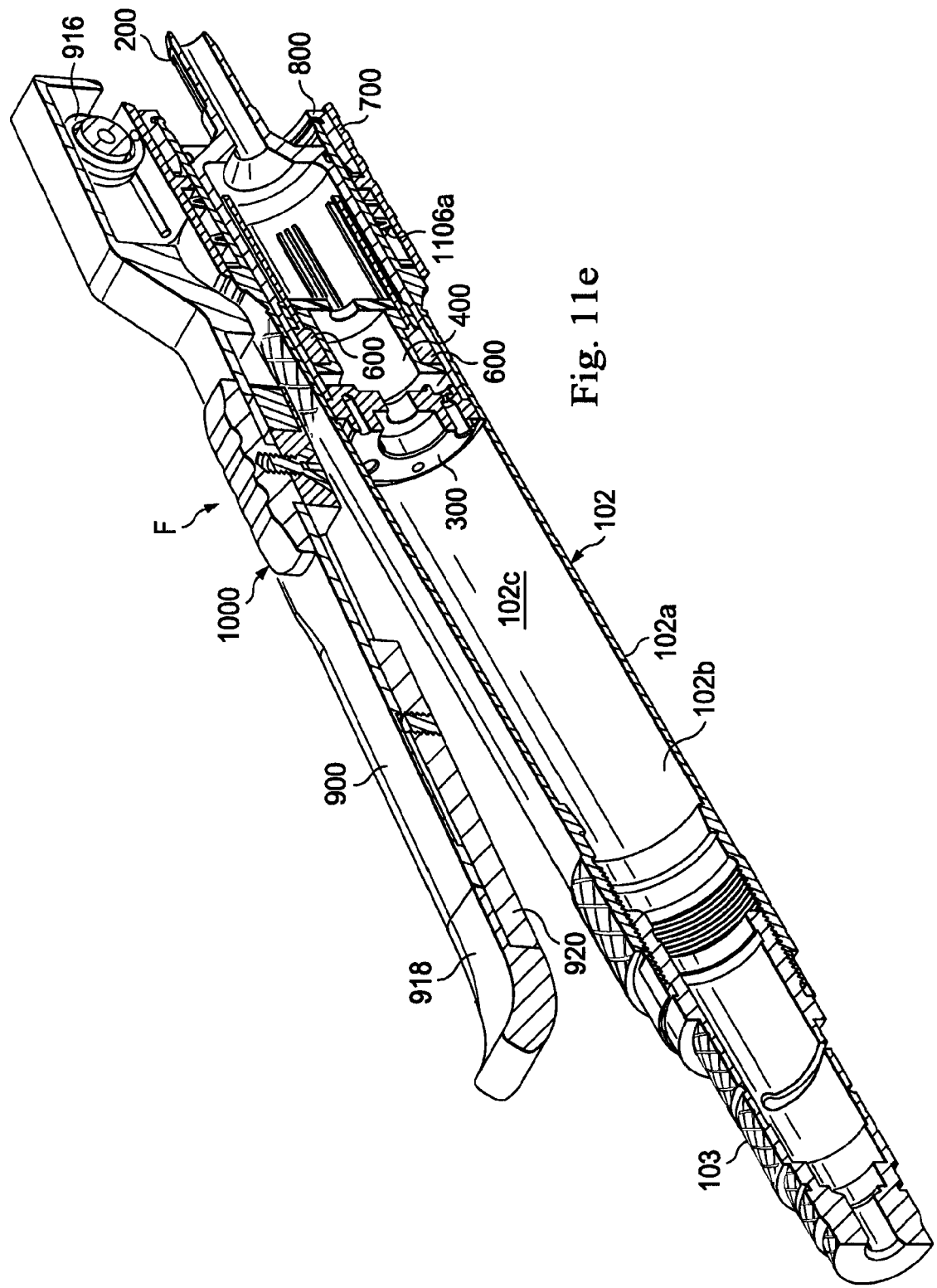
FIG. 11e is a cross sectional view illustrating an embodiment of the switch on the surgical instrument moved into a second switch orientation.

Referring now to FIGS. 1b, 1c, 1d, 11a, 11b, and 11c, a method 1100 for controlling a surgical instrument is illustrated. The method 1100 begins at block 1102 where the surgical instrument 100 is provided. In an embodiment, the collar 700 on the surgical instrument 100 is positioned in an orientation A such that the actuator 1018 in the switch 1000 on the lever 900 is aligned with one of the sensors 600, illustrated in FIG. 1c, with the resilient member 916 biasing the lever 900 and the actuator 1018 away from the housing 102 and the sensor 600, respectively. The method 1100 then proceeds to block 1104 where the lever 900 is pivoted to produce a signal from one of the sensors 600. A user of the surgical instrument 100 may apply a force to the lever 900 to move the lever in a direction B, illustrated in FIG. 1c, such that the actuator 1018 is moved towards the sensor 600. In an embodiment, the sensor 600 is a Hall-effect sensor and the actuator 1018 is a magnet, and the movement of the actuator 1018 relative to the sensor 600 will vary a signal produced by the sensor 600. For example, as the magnet actuator 600 is moved towards the Hall-effect sensor 600, the Hall-effect sensor 600 will detect the gauss field strength of the magnet actuator 600 and provide a variable voltage signal which is read by control circuitry and used to increase the motor speed and the speed of the cutting tool 104a. With the lever 900 fully pivoted such that the lever 900 is immediately adjacent the housing 102 and the actuator 1018 is adjacent the sensor 600, as illustrated in FIGS. 1d, 11c, and 11b, the signal sent from the sensor 600 will result in the motor supplying the maximum amount of speed allowed to the cutting tool 104a. In an embodiment, when the user of the surgical instrument 100 releases the lever 900, the resilient member 916 will resiliently bias the lever 900 and the actuator 1018 away from the housing 102 and the sensor 600, respectively, which will vary the signal that is produced by the Hall-effect sensor 600 and sent to the motor (not shown) to decrease the speed of the motor and the speed of the cutting tool 104a.

Referring now to FIGS. 1b, 1c, 1d, 11a, 11b, and 11c, the method 1100 proceeds to blocks 1106 and 1108 where the collar 700 is rotated and the lever 900 is pivoted to produce a signal from a different sensor 600 than the sensor 600 that produced the signal in block 1104 of the method 1100. As described above, in an embodiment, the collar 700 is moveably coupled to the housing 102 such that the collar 700 may rotate about the housing 102 into a plurality of different, discrete orientations. In the illustrated embodiment, a crest-to-crest wave spring 1106a provides tension to keep the collar 700 and the press ring 800 engaged. To rotate the collar 700, the collar 700 is pulled or pushed along the length of the housing 102 and away from the press ring 800 to disengage the collar 700 from the press ring 800, rotated (e.g. by 90 degrees), and then released to allow the tension from the crest-to-crest wave spring 1106a to re-engage the collar 700 and the press ring 800. As such, the collar 700 may be rotated about the housing 102 into an orientation C such that the actuator 1018 in the switch 1000 on the lever 900 is aligned with one of the sensors 600 and may be moved relative to the sensor 600 to produce a signal from that sensor 600, as illustrated in FIG. 11d. In an embodiment, the collar 700 may be rotated about the housing 102 into any orientation corresponding to a sensor 600 in order to allow the lever 900 to be pivoted to vary the motor speed and the speed of the cutting tool 104a. Thus, a surgical instrument 100 is provided that includes a lever and actuator that may be moved about the housing of the surgical instrument 100 to avoid obstructions or to ease user fatigue.

Figure 11F:
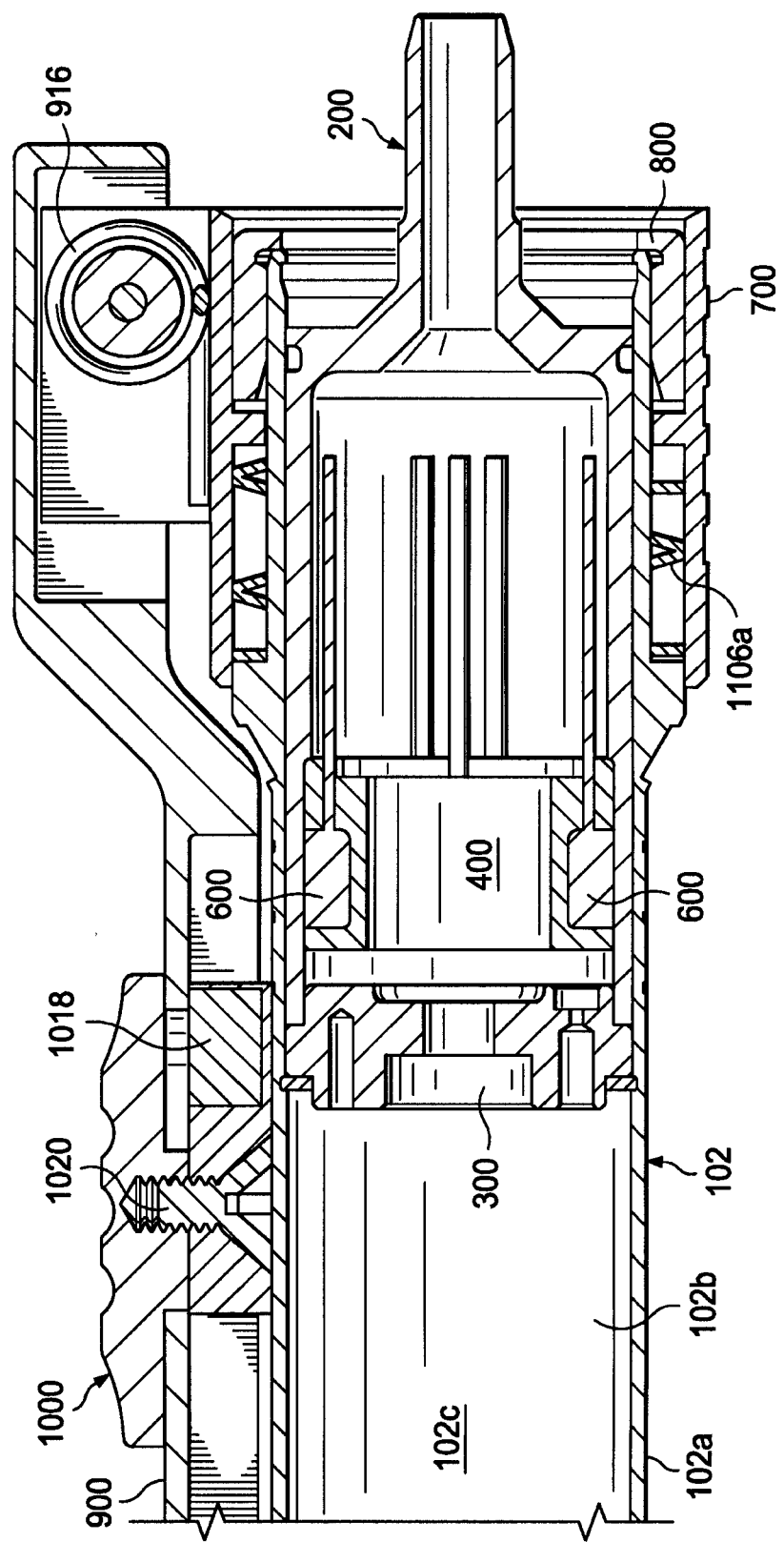
FIG. 11f is a cross sectional view illustrating an embodiment of the switch on the surgical instrument moved into a second switch orientation with the lever pivoted towards the housing.

Referring now to FIGS. 1b, 1c, 1d, 11a, 11e and 11f, the method 1100 proceeds to block 1110 where the switch 1000 is moved to prevent signal production. With the collar 700 in any orientation corresponding to a sensor 600 such as, for example, the orientation A illustrated in FIG. 1c, the switch 1000 may be moved in a direction D from a first switch orientation E, illustrated in FIG. 1c, to a second switch orientation F, illustrated in FIG. 11e, where the actuator 1018 has been translated along the length of the lever 900. When the lever 900 is then pivoted, as described above with reference to block 1104 of the method 1100, the actuator 1018 will not be located adjacent the sensor 600, as illustrated in FIG. 11f, and the signal from the sensor 600 will not be varied such that the motor will not vary the speed of the cutting tool 104a.

Figure 11G:
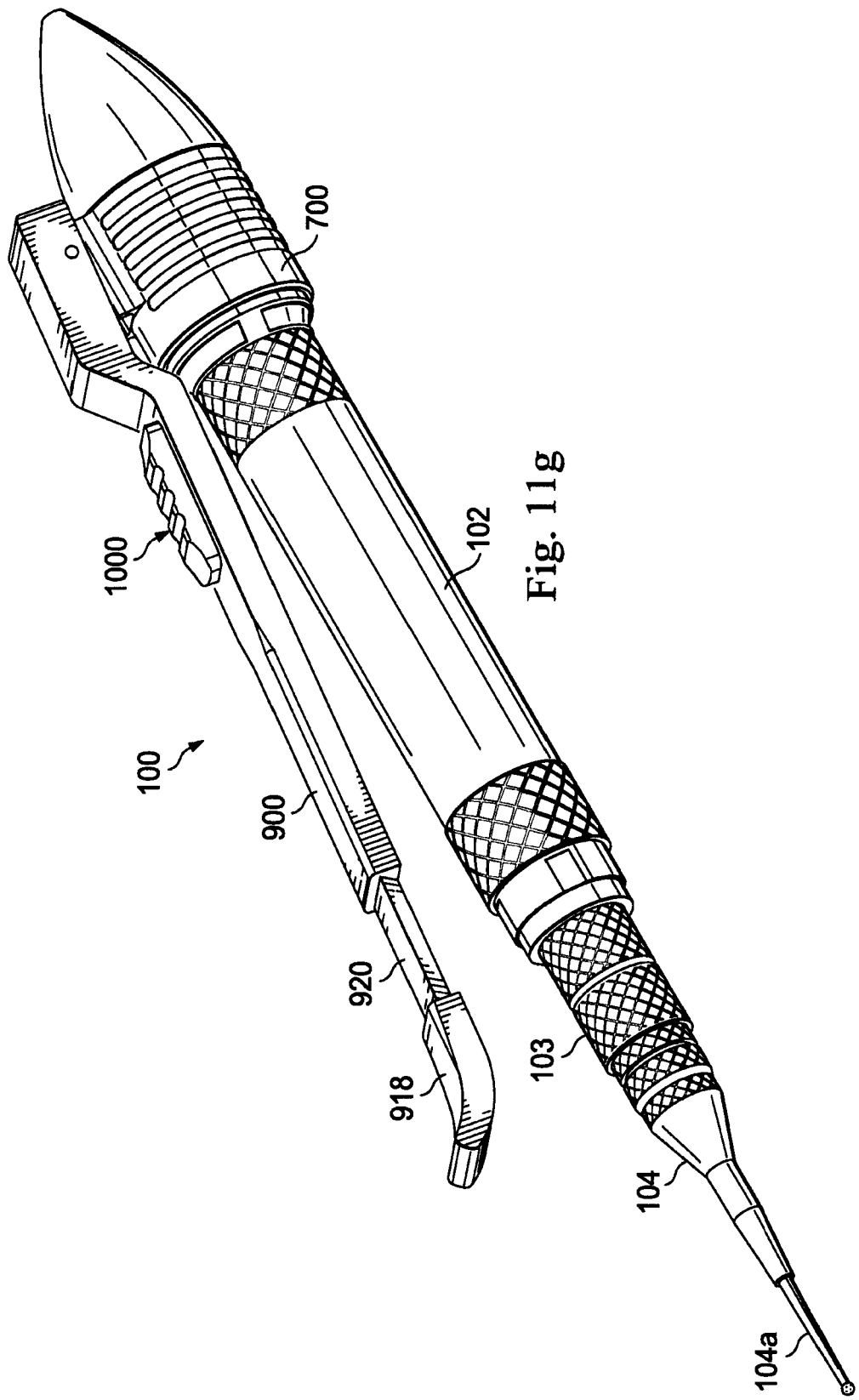
FIG. 11g is a perspective view illustrating an embodiment of the distal end of the lever extended.
Figure 11H:
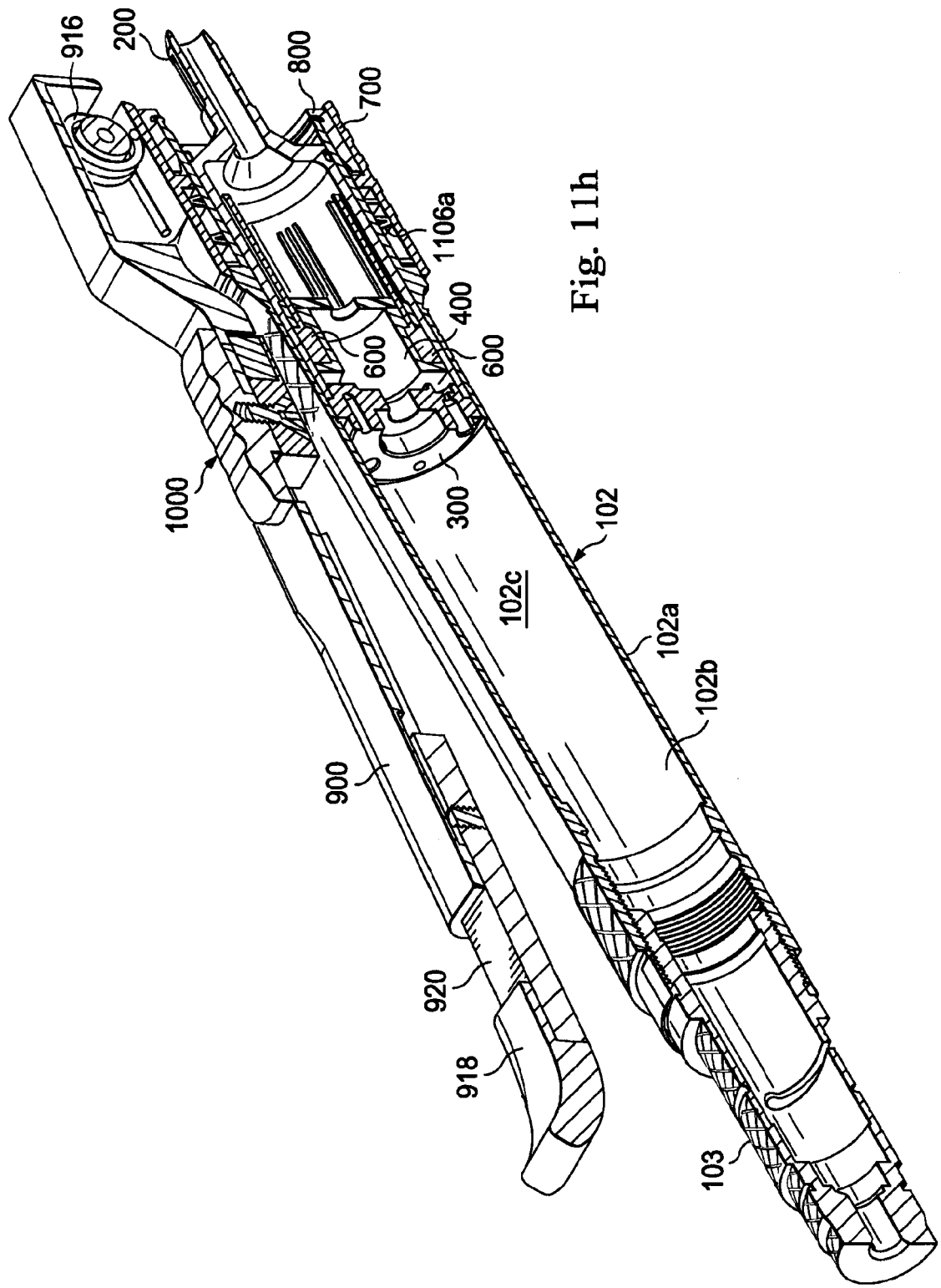
FIG. 11h is a perspective, cross sectional view illustrating an embodiment of the distal end of the lever extended.

Referring now to FIGS. 1b, 1c, 1d, 11a, 11g, and 11h, the method 1100 proceeds to block 1112 where the distal end 918 on the lever 900 is extended. The slidable coupling 920 allows the distal end 918 to be extended from the lever 900 to effectively increase the length of the lever 900, as illustrated in FIGS. 11g and 11h.

While the invention has been particularly shown and described with reference to the preferred embodiment thereof, it will be understood by those skilled in the art that various changes in form and detail may be made therein without departing from the spirit and scope of the invention. Furthermore, the housings and/or components may be replaced by other suitable elements to achieve similar results. In addition, a variety of materials may be used to form the various components and the relative sizes of components may be varied. Therefore, the claims should be interpreted in a broad manner, consistent with the present invention.

What is claimed is:

1. A control for a powered surgical instrument, the control comprising:
   a housing;
   a plurality of sensors located in the housing in a spaced apart orientation from each other; and
   a lever pivotal relative to the housing and moveable about the housing into a plurality of different radial orientations, wherein each of the plurality of different radial orientations corresponds to a respective one of the plurality of sensors, the lever comprising an actuator wherein, with the lever located in any one of the plurality of different radial orientations, the lever is operable to move the actuator relative to the respective one of the plurality of sensors in order to vary a signal that is produced by that sensor due to the relative movement of the actuator.

2. The control of claim 1, wherein the plurality of sensors are located adjacent an inner surface of the housing in a radially spaced apart orientation from each other.

3. The control of claim 2, wherein the plurality of sensors are radially spaced apart by approximately 90 degrees.

4. The control of claim 1, further comprising a collar rotatably attached to the housing and operable to be indexed into a plurality of different collar orientations, the lever being carried on the collar.

5. The control of claim 4, wherein the lever is resiliently and pivotally coupled to the collar.

6. The control of claim 1, further comprising:
a switch moveably coupled to the lever, wherein the actuator is located on the switch.

7. The control of claim 6, wherein the switch comprises a first switch orientation on the lever in which movement of the lever relative to one of the plurality of sensors varies a signal produced by that sensor, and a second switch orientation on the lever in which movement of the lever relative to one of the plurality of sensors does not vary a signal produced by that sensor.

8. The control of claim 1, further comprising:
a distal end on the lever, wherein the distal end is extendable from the lever to increase the length of the lever.

9. A powered surgical instrument, comprising:
a housing;
a motor housed in the housing;
at least one sensor disposed in the housing and configured to generate a signal to increase and decrease the operating speed of the motor; and
a lever pivotally connected to the housing and comprising a switch and an actuator, the switch being configured to displace the actuator along the lever from a first orientation on the lever in which movement of the lever relative to the at least one sensor varies a signal produced by the at least one sensor, and a second orientation on the lever in which movement of the lever relative to the at least one sensor does not vary a signal produced by the at least one sensor.

10. The instrument of claim 9, wherein said at least one sensor comprises a plurality of sensors coupled to the motor and housed in the housing in a spaced apart orientation from each other, the lever being disposable in a plurality of different orientations that respectively align with different sensors of the plurality of sensors.

11. The instrument of claim 10, further comprising a collar mounted to and rotatable about the housing into a plurality of discrete collar orientations, and wherein each discrete collar orientation corresponds to a respective one of the plurality of sensors, wherein the lever is carried on the collar in a manner that aligns the actuator with a different respective sensor of the plurality of sensors for each of the plurality of discrete collar orientations.

12. The instrument of claim 10, wherein the plurality of sensors are located adjacent an inner surface of the housing in a radially spaced apart orientation from each other.

13. The instrument of claim 12, wherein the plurality of sensors are radially spaced apart by approximately 90 degrees.

14. The instrument of claim 9, wherein the actuator is disposed adjacent a proximal end of the switch.

15. The instrument of claim 9, further comprising:
a distal end on the lever, wherein the distal end is extendable from the lever.

16. A method for controlling a surgical instrument, the method comprising:
providing a surgical instrument comprising a housing and a lever pivotably and rotatably associated with the housing, the lever comprising an actuator, wherein the lever is located in a first radial orientation relative to the housing, and wherein the first radial orientation corresponds to a first sensor in the housing;
pivoting the lever to move the actuator relative to the first sensor in order to vary a signal that is produced by the first sensor due to the relative movement of the actuator;
rotating the lever into a second radial orientation on the housing, wherein the second radial orientation corresponds to a second sensor in the housing; and
pivoting the lever to move the actuator relative to the second sensor in order to vary a signal that is produced by the second sensor due to the relative movement of the actuator.

17. The method of claim 16, further comprising:
extending a distal end of the lever.

18. The method of claim 16, wherein the lever is connected to a collar rotatable about the housing, and wherein rotating the lever comprises rotating the collar away from a position where the lever is aligned with the first sensor and into a position where the lever is aligned with the second sensor.

19. The method of claim 16, wherein the varying of signals produced by the first sensor and the second sensor result in the varying of a speed of a cutting tool that is coupled to the housing.

20. The method of claim 16, further comprising:
moving a switch that includes the actuator and that is coupled to the lever, wherein the moving of the switch prevents the varying of a signal produced by the first sensor or the second sensor when the actuator is moved relative to that sensor.

* * * * *